(12) United States Patent
Laserow

(10) Patent No.: US 6,709,406 B2
(45) Date of Patent: *Mar. 23, 2004

(54) MEASUREMENT OF PAIN

(75) Inventor: Kay Laserow, Malmo (SE)

(73) Assignee: Cefar Matcher AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/927,308

(22) Filed: Aug. 13, 2001

(65) Prior Publication Data

US 2001/0049472 A1 Dec. 6, 2001

Related U.S. Application Data

(63) Continuation of application No. 09/506,374, filed as application No. PCT/SE96/01668 on Dec. 18, 1996, and a continuation of application No. 09/091,817, filed on Sep. 21, 1998, now Pat. No. 6,146,334.

(51) Int. Cl.$^7$ .................................................. A61B 5/00
(52) U.S. Cl. ........................................................ 600/552
(58) Field of Search ................................ 600/552, 555, 600/557, 554, 551, 382; 606/27, 29, 20; 607/96; 128/630, 744, 742, 741

(56) References Cited

U.S. PATENT DOCUMENTS

| | | | | |
|---|---|---|---|---|
| 4,557,273 A | * | 12/1985 | Stoller et al. | 600/551 |
| 4,763,666 A | * | 8/1988 | Strian et al. | 600/554 |
| 5,007,433 A | * | 4/1991 | Hermsdorffer et al. | 600/555 |
| 5,191,896 A | * | 3/1993 | Gafni et al. | 600/555 |
| 5,634,472 A | * | 6/1997 | Raghuprasad | 600/555 |
| 6,387,054 B1 | * | 5/2002 | Laserow | 600/552 |

* cited by examiner

*Primary Examiner*—Max F. Hindenburg
*Assistant Examiner*—Brian Scott Szmal
(74) *Attorney, Agent, or Firm*—Oblon, Spivak, McClelland, Maier & Neustadt, P.C.

(57) ABSTRACT

The invention relates to a measuring instrument for the measurement of an existing pain or a feeling of nausea of a patient. The measuring instrument induces pain in an arbitrary body part of said patient, by supplying an electrical current. The measuring instrument provides a current increase into said body part, until said induced pain is experienced by the patient as being as great as the existing pain/nausea. The current is supplied from a current source arranged in the measuring instrument via wires (H, I) and electrodes (C, D), said electrodes being applied onto that part of the body in which pain is to be induced. When the pain induced is experienced to be as great as the existing pain/nausea, the body part is removed from the electrodes, whereupon a pain value is registered and shown on a display (F).

36 Claims, 3 Drawing Sheets

MEASUREMENT OF PAIN

AREA OF THE INVENTION

The present invention relates to a measuring instrument and a method of measuring, by means of the instrument, an existing pain experienced by a patient.

STATE OF THE ART

When a person in need of medical treatment first comes into contact with a doctor, a physiotherapist, a nurse etc., this person generally tries to describe his pain verbally, so that the medical staff are at least able to make a primary diagnosis of the patient's condition and suggest a suitable treatment. However, this creates a significant problem for the medical staff, depending upon different persons experiencing, and therefore describing, their pain or symptoms in different ways. One person may e.g. be more resistant to pain than others. Another person may e.g. have become used to his pain after a certain period of time and may therefore describe his/her pain in milder terms than he/she would have done if the pain had arisen recently. The varying descriptions of pain which a diagnostician may be exposed to complicate a quick and exact diagnosis of a person's ailment or injury.

For the sake of simplicity, in the below text the patient is always referred to as being male. It should of course be understood, however, that the same applies to female patients.

In order to hitherto measure pain in patients, doctors, physiotherapists etc. use a so called measuring rod or ruler; this technique is called Visual Analogue Scale (VAS). The general design of a measuring rod having a VAS scale is shown in FIGS. 1 and 2. There is, however, a variety of different designs of this measuring rod, but their function is generally the same and will be described with reference to FIGS. 1 and 2.

As can be seen from FIG. 1, the measuring rod is divided into grades from e.g. 0–10, where "0" means no sensation of pain and where "10" means unbearable sensation of pain or worst possible sensation of pain. FIG. 2 shows the reverse side of the measuring rod of FIG. 1, and during a measurement the patient will only see this side.

Suppose a patient having a pain in his arm goes e.g. to a doctor. The doctor picks up his ruler (measuring rod) and asks the patient if he can describe his sensation of pain by placing his finger on that spot on the ruler which best corresponds to the sensation of pain in his arm. The doctor has of course previously explained to the patient how the ruler functions, i.e. that one end A of the ruler corresponds to no sensation of pain and the other end B of the ruler corresponds to an unbearable sensation of pain (FIG. 2).

Assume that the patient places his finger on the ruler at a value of "7" on the pain scale (0–10). The scale on the ruler is turned towards the doctor so that only he can see the pain scale (FIG. 1) and the patient can only see the reverse side of the ruler as shown by FIG. 2.

The doctor thus quickly obtains information about how the patient at present subjectively experiences the pain in his arm.

The doctor then prescribes a treatment for the patient, e.g. some kind of painkiller.

When the patient comes for his next visit to the doctor, the same procedure with the ruler is repeated, and the patient now places his finger at a location on the ruler which e.g. corresponds to the value "2" on the pain scale (0–10).

The doctor thus obtains an indication that the pain in the arm has decreased by comparing the previous value of "7" with the present value of "2". Thus, the doctor can conclude that the treatment has been effective.

If the patient during his next visit instead places his finger at a location on the ruler which e.g. corresponds to the pain value of "8,5", the doctor can instead determine that the previous treatment has been ineffective, and he can therefore act accordingly; e.g. prescribe a new medicine or a referral to a physiotherapist, a masseur etc. The doctor thus uses the measuring rod to determine whether a treatment has been effective or not.

One problem with this ruler according to FIGS. 1 and 2 is that the patient must consciously think about and evaluate where to place his finger on the ruler, between the values no sensation of pain and unbearable sensation of pain, as shown in FIG. 2. The patient is all the time aware of, that the closer he places his finger in relation to the end A of the ruler, i.e. no sensation of pain, the less pain he is supposed to sense, and the closer he places his finger in relation to the end B of the ruler, i.e. unbearable sensation of pain, the more pain he is supposed to sense. This awareness of the patient is just what the present invention eliminates.

Another problem with the ruler according to FIGS. 1 and 2 is that the doctor cannot objectively verify the pain value given by the patient; the patient may e.g. lie about his sensation of pain and place his finger at the same pain value at different measurement occasions.

A further problem with the ruler according to the FIGS. 1 and 2 is that different persons sense pain in different ways. Some persons can stand pain better than others and will describe their pain with a low value (e.g. "2") on the ruler; other persons have a low pain threshold and will describe the same pain with a high value (e.g. "9") on the ruler.

The present invention also eliminates this problem.

In order to find out if the previous art solves the problems mentioned above, a pre-study was performed, whereby the following documents were found.

The document EP,B1 0 438 541 describes a portable instrument performing a multidimensional indication of pain sensed by a person. The portable instrument has indicators that may be adjusted by a person to provide a physical indication of the type of pain intensity being sensed by said person.

The document U.S. Pat. No. 4,641,661 describes an electronic meter for determining the pain threshold for a pressure applied to the skin surface of a patient. The pressure is increased until the patient presses a button when he/she senses pain. The pressure achieved is registered.

The document U.S. Pat. No. 4,697,599 describes a device for localisation and detection of pain by measurement of the conductivity of the tissue.

The document U.S. Pat. No. 5,020,542 shows a method for measuring the sensibility of the skin of a patient to electrical stimulation.

The document JP,7 023 964 describes a method for measuring pain objectively and quantitatively.

The document GB,2 049 431 describes a so called measuring rod for providing a subjective measurement of the pain sensed by the patient.

The documents found do not solve the problems mentioned above.

SUMMARY OF THE INVENTION

Thus, the object of the present invention is to solve the above problems.

Another object of the present invention is to allow an objective way of performing the pain measurement.

Yet another object of the present invention is to provide a measurement value of pain which is relevant for comparison between different patients.

A further object of the present invention is to provide a portable, very easy to use, measuring instrument for the measurement of pain.

Yet a further object of the present invention is to allow the doctor, the physiotherapist etc. to feel and sense the patient's pain, which has a psychological significance that may entail a shortened time for medical care of the patient, as the patient feels he has been understood.

These objects are achieved by a device and a method according to the characterizing parts of the appended patent claims, respectively.

Advantageous embodiments of the present invention are described in the dependent claims.

Detailed embodiments of the present invention will now be described with reference to the enclosed drawings.

SHORT DESCRIPTION OF THE DRAWINGS

DETAILED DESCRIPTION OF EMBODIMENTS OF THE INVENTION

In the following, each of the embodiments mentioned according to FIGS. 3–10 will be discussed. The first embodiment of the invention will be described in more detail, as this embodiment will also describe the idea of the invention by means of an example.

The other embodiments are based on the same inventive idea.

Figure 3:
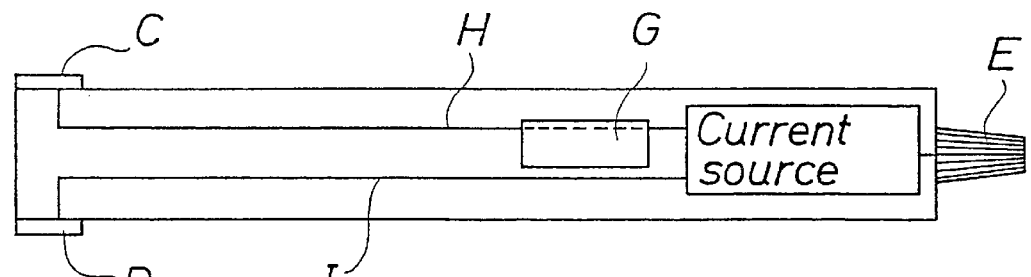
FIG. 3 shows a cross sectional view from above of a first embodiment of the measuring instrument according to the invention.
Figure 4:
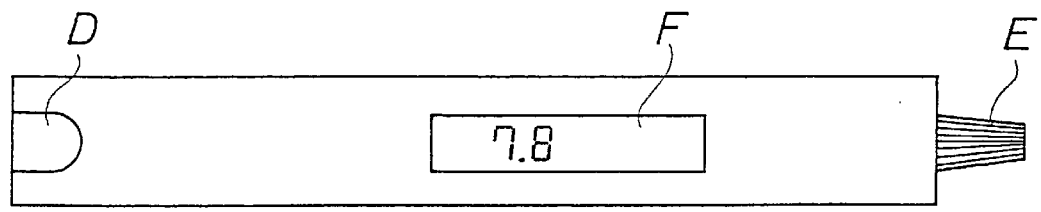
FIG. 4 shows a side view of the measuring instrument of FIG. 3.

Referring now to FIGS. 3 and 4, two electrodes C and D are attached, one on each side, at one end of the measuring instrument. The electrodes are connected by wires I and H to a current source, where the current is controlled by a control knob E.

At one side of the measuring instrument there is a display F, capable of showing, e.g. digitally, a value of e.g. 0–10. This value is of course intended for indication, in the same way as before, of a degree of pain sensed, where the value "0" corresponds to a total absence of pain and the value "10" corresponds to an unbearable pain.

Furthermore, there is a memory register G for storage of an arbitrary number of pain readings (0–10).

The present invention will now be described by way of an example, with reference to FIGS. 3 and 4.

Assume that a patient having pains in his arm comes to a doctor. The doctor produces his measuring instrument according to the first embodiment, and asks the patient to take a steady grip with e.g. his index finger and thumb around the electrodes C and D.

The doctor now informs the patient that a current will be supplied to the electrodes, the increase of which will be controlled by the doctor via the control knob E. The doctor further informs the patient that he will sense a pain in the index finger and thumb that are grasping the electrodes C and D; as the current increases, the pain in the fingers will increase accordingly. The doctor now informs the patient that he should release the grip around the electrodes C and D when the pain in his fingers is experienced to be as great as the pain in the bad arm.

The doctor thus increases the current through the wires H and I with the control knob E, and when the patient senses that the pain in his fingers is as great as the pain in the bad arm he releases his grip around the electrodes C and D, whereupon a pain reading, e.g. "7.8" is registered in the memory G and is displayed digitally on the display F. This pain value is of course proportional to the magnitude of the current.

When the patient returns after treatment, the same procedure is repeated, whereupon the pain reading "2" is registered. Thus, the doctor now knows, in the same manner as before, that the treatment has been effective.

Figure 1:
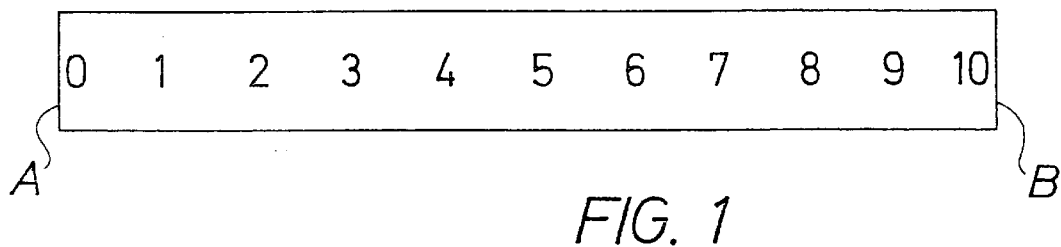
FIG. 1 shows a principle design of a measuring rod (ruler) according to the state of the art, seen from the front.
Figure 2:
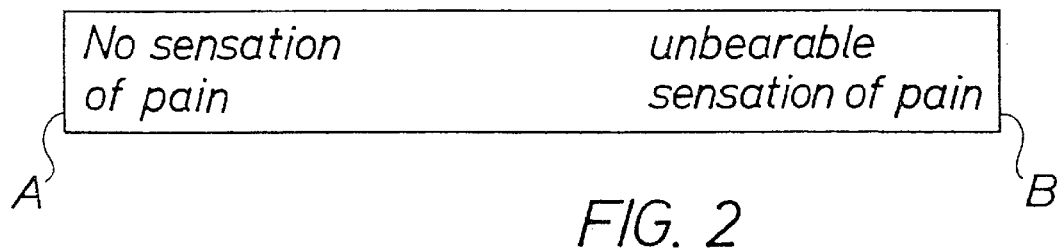
FIG. 2 shows the measuring rod of FIG. 1 seen from the rear.

The above described measuring instrument according to the present invention however differs markedly from the earlier measuring rod according to FIGS. 1 and 2, through the patient associating, by means of the measuring instrument according to the present invention, a pain (in his fingers) with another pain (in his bad arm).

The patient thus releases the grip around the electrodes C and D when the pain in his fingers is experienced as being as great as the pain in his arm, and the patient thus has no idea about which pain reading on the scale (0–10) he causes.

When the patient uses the measuring instrument according to the present invention, he will not refer to any greatest (unbearable sensation of pain) or smallest (no sensation of pain) pain value as with the measuring rod according to FIGS. 1 and 2.

The pain measurement according to the present invention is thus objective in the sense that the patient cannot consciously determine what pain value he will obtain, as it is the comparison between the pain in his fingers and the pain in his arm that is his reference, not any visual pain scale.

Furthermore, as a given pain value corresponds to a given current level, pain values between different patients can be compared. It is thus possible, based on the pain values, to determine objectively that a certain patient will endure greater pain than another patient; this is e.g. not possible with the measuring rod according to FIGS. 1 and 2. With the measuring instrument according to the present invention the doctor can easily check if the patient is "lying" about his pain by performing an arbitrary number of measurements and comparing the pain values from the different measurements; if approximately the same pain value is obtained throughout all measurements it can be regarded as reasonable that the patient speaks the truth.

The doctor can also experience the pain which the patient senses, by grasping the electrodes C and D; this may be of psychological importance to the patient and entail a shortening of his time in medical care.

Figure 5:
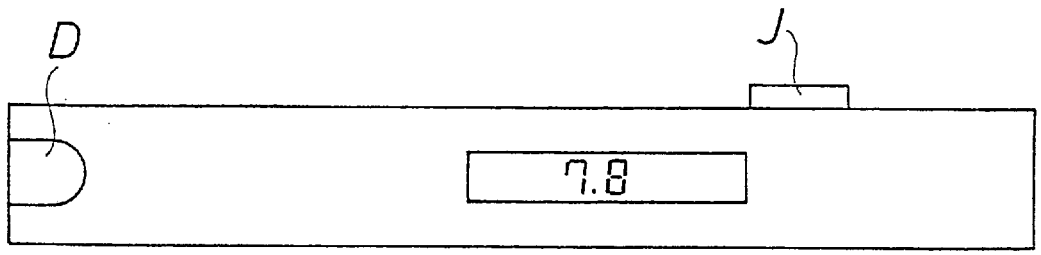
FIG. 5 shows a second embodiment of the measuring instrument according to the invention.

FIG. 5 shows a second embodiment of the measuring instrument according to the invention. This embodiment differs from the measuring instrument in FIGS. 3 and 4 only by the current to the electrodes C and D being increased by means of a push-button J.

By depressing this button J, the current is thus increased in an arbitrary, predetermined fashion; for example 50 $\mu$A upon each depression.

Figure 6:
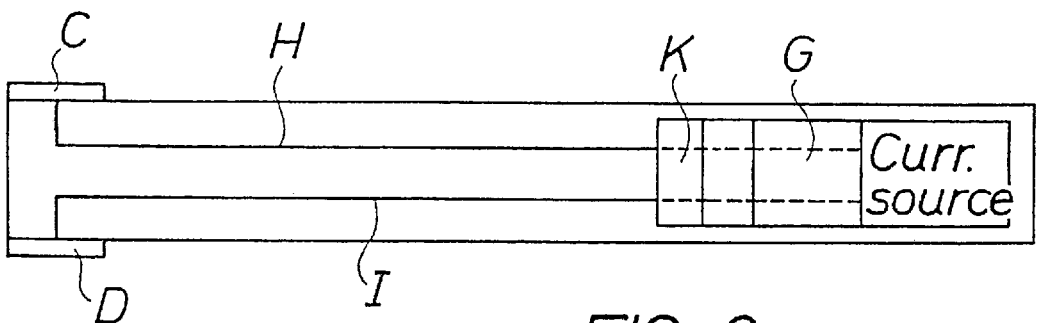
FIG. 6 shows a cross sectional view from above of a third embodiment of the measuring instrument according to the invention.
Figure 7:
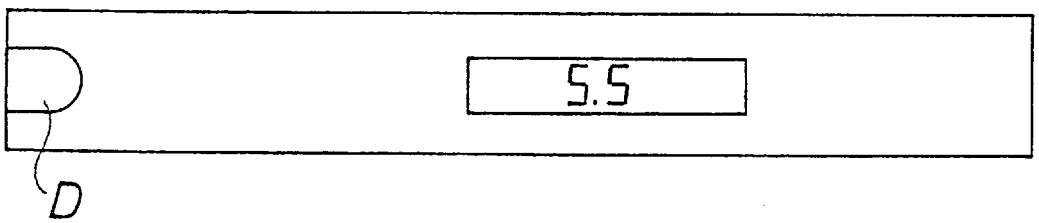
FIG. 7 shows a side view of the measuring instrument of FIG. 6.

The FIGS. 6 and 7 show an especially preferred embodiment of the measuring instrument. This embodiment functions in such a way that when e.g. the thumb and the index finger grasp around the electrodes C and D, a current circuit is closed, whereby a current flows from the current source via the wire H and the electrode C through the thumb and the index finger, and back to the current source via the electrode D and the wire I. The current increases automatically by steps of e.g. 50 $\mu$A, being controlled by a microprocessor K. Furthermore, the microprocessor may be programmed so as to control the current increase in a linear or exponential manner. The microprocessor also controls the time it will take for the current to increase from a minimum current to a maximum current.

When the current has increased to such an extent that the patient experiences the pain in his thumb and index finger to be as great as the pain in e.g. his bad arm, the patient releases his grip around the electrodes C and D, whereupon the current circuit is interrupted, and the current value is registered, in the same manner as before, in the memory G and shown on the display F. This measuring instrument according to FIGS. 6 and 7 is thus very easy to handle and user friendly, as it only needs for the patient to grasp with his thumb and index finger around the electrodes C and D, whereupon the current increase takes place fully automatically. The measuring instrument according to FIGS. 6 and 7 may also be equipped with a stop button (not shown) for stopping the automatic current increase. When the patient depresses this stop button, the automatic current increase will stop, causing the current source only to feed a constant current, corresponding to the current flowing immediately before the stop button was depressed.

This stop button may be used, for example, when the doctor wants to experience the current strength that the patient senses. This is thus performed through the patient stopping the current increase when the existing pain (e.g. his bad arm) is experienced as being as great as the pain caused by the current, by depressing the stop button, whereupon the doctor grasps, with his fingers, around the electrodes C and D. It may, as mentioned before, have a certain psychological impact that the doctor can experience the patient's pain, as the patient may then feel understood. If the stop button is depressed again, the current will resume its automatic increase.

Figure 8:
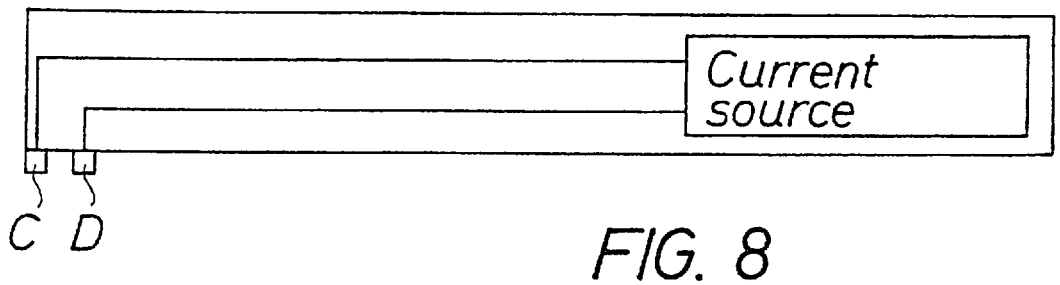
FIG. 8 shows a cross sectional view from above of a fourth embodiment of the measuring instrument according to the invention.

FIG. 8 shows a fourth embodiment of the measuring instrument. This measuring instrument in principle functions in the same manner as the measuring instrument of FIGS. 6 and 7; the current will increase automatically when the current circuit is closed (i.e. when the electrodes C and D are short-circuited).

This measuring instrument however differs from the earlier described measuring instruments by having its electrodes C and D arranged in such a manner as to be applicable anywhere on the body. This measuring instrument is especially advantageous for use with extremities which are paired, e.g. arms, legs, ears, etc.

Assume for example that a patient has a pain in his left knee. The doctor then applies the electrodes C and D of the measuring instrument according to FIG. 8 onto the patient's right knee, whereupon pain is also induced in this knee. The measuring instrument according to FIG. 8 thus utilises the principle that it is easier for a patient to associate a pain in his left knee with a pain in his right knee; it is easier to compare pain sensations in similar body parts. The sensation of pain in each side of the body is transferred independently to the brain. Consequently, the sensitivity in a certain area of the body can be compared to that in a reference area on the opposite side thereof.

In the embodiments of the measuring instrument according to the present invention, it should be understood that it is also possible to reduce the current via the push-button J or the control knob E. In one embodiment of the present invention it will be possible to combine the automatic current increase and the stop button with the push-button J or the control knob E.

It will also be possible for a patient to perform the pain measurement himself, in the absence of a doctor, physiotherapist, etc. In this case, the pain values are not shown on the display F but are only stored in the memory G, so as not to inform the patient about them. The doctor may subsequently, by means of a certain button (not shown) retrieve these values from the memory G and show them on the display means.

The memory G will be designed so that arbitrary information, such as e.g. time, date, various patient names with their respective series of pain values etc., may be stored. There will also be a possibility for printing out this information on e.g. a strip of paper.

Figure 9:
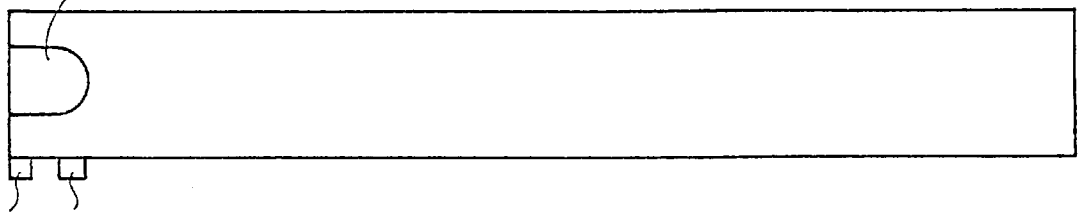
FIG. 9 shows a fifth embodiment of the measuring instrument according to the invention.

FIG. 9 shows an especially preferred embodiment of the measuring instrument which is a combination of the measuring instrument of FIGS. 6 and 7 and the measuring instrument of FIG. 8. This measuring instrument is thus designed on the one hand to be grasped around the electrodes L and M with the fingers, on the other to be applicable onto an arbitrary body part via the electrodes N and O, in the same way as described before.

In order for the patient to receive adequate pain stimulation in the body part which is touched by the electrodes, it is necessary to secure a predetermined minimum pressure against the electrodes.

One way of achieving this is to see to it that this predetermined minimum pressure corresponds to the force required to grasp the electrodes C and D by the thumb and index finger and at the same time to hold the measuring instrument in a horizontal position. In this case it will be required that a string is attached to an arbitrary position on the measuring instrument, whereby e.g. the doctor holds the other end of the string, to prevent the instrument from falling to the floor when the patient releases the electrodes C and D. If the doctor is increasing or decreasing the electrode current manually, in this case, when the measuring instrument is in a horizontal position, an external hand-held control is required. The hand-held control is then connected to the measuring instrument by a wire and thus replaces the push-button J and the control knob E. If the current increase is automatic, naturally no external hand-held control is necessary.

Figure 10:
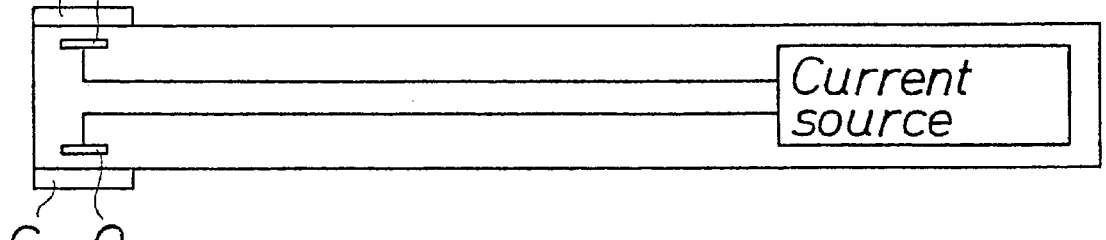
FIG. 10 shows a cross sectional view from above of a sixth embodiment of the measuring instrument according to the invention.

Yet another method for arranging this predetermined minimum pressure on the electrodes is to use a resilient contact as shown in FIG. 10. In this case, the electrodes must be pressed inwards until they touch the contacts P and Q, whereby the current circuit is closed. This pressure for closing the circuit is consequently so matched as to achieve an adequate pain stimulation.

It should be understood that the measuring instrument according to the embodiments described above is a portable instrument that can easily be carried by e.g. a doctor. The length of the instrument will principally correspond to the length of the previous measuring rod. However, the instrument will be somewhat thicker than the previous measuring rod, as this instrument has to contain a certain amount of electronics.

The measuring instrument preferably comprises at least a battery, a means of upwards transformation of voltage, a microprocessor for display control etc., and possibly memory circuits. The pain scale to be utilised preferably runs from 0,0–9,9, 0–60 or 0–99.

It has been shown, empirically, that the pain measurements with this measuring instrument functions in a very satisfactory way when the following measurement method is used:

- the patient grasps around the electrodes (C, D) with his right thumb and index finger;
- the current is increased automatically when the circuit is closed (alternatively, the patient has to press the start button in order to start the automatic current increase);
- when the pain in his fingers is experienced as being as great as his existing pain in e.g. a knee, the patient depresses the stop button. The automatic current increase ceases and the stimulation remains constant. The patient will at this point try "once extra", that the pain in his fingers is as great as the existing pain;
- the patient then releases his tweezers grip around the electrodes (C, D). If the patient thinks the pain in his fingers is lower than the existing pain, he may push the stop button again, making the current increase automatically, etc. It is thus not until the patient releases his tweezers grip (open circuit), that the measurement is terminated;
- the doctor depresses the value button, the pain value is shown on the LCD, and the pain value is noted down.

It is to be understood that the stop button is arranged at such a location on the measuring instrument as to be easily accessible for the patient.

It is further foreseen that the measuring instrument (the pain meter) will be used for pain measurements outside the hospital. A large application area is pain measurement during studies of pharmaceutical drugs. The pain meter must then follow the patient 24 hours/day.

The patient will perform the pain measurement himself as described above, with the difference that upon a finished measurement, the pain value is saved in a memory and the pain meter is switched off automatically. The patient consequently will not see the measured pain value. After e.g. four weeks the patient goes to see his doctor. The doctor takes the pain meter and connects it to a computer, preferably via an interface. The saved pain values are transferred to the computer for further analysis/processing. Examples of data saved are patient name/birth data, date (each measurement), time (each measurement), and pain value (each measurement). It is also conceivable that the pain meter includes a system for making the patient aware of that it is time to perform a measurement, or that the pain meter is integrated into a system where this function is available.

In the foregoing, we have only discussed a comparison between an induced pain and an existing pain. It is of course to be understood, that the measuring instrument according to the invention may be used to compare an induced pain with, in general, an arbitrary feeling. If, for example, a patient feels ill at ease, this feeling may be compared with a pain induced into the patient by means of the measuring instrument. The invention is especially intended for also allowing the comparison between a pain induced by the measuring instrument and sensations of nausea. It is to be understood that in the concept of pain, we also include unpleasant sensations.

The quintessence of the present invention, however, is that the patient receives a physical stimulus (electrical current) into a part of his body, and compares said induced pain in this body part with an existing pain (e.g. his bad arm) or with a feeling of nausea. When the induced pain in the body part coincides with the existing pain/nausea sensation, the pain value is registered through the patient actively causing the induced pain to cease.

In this way the pain may be objectively graded, with the physical stimulus (the current) as reference, i.e. there is no reference to any fixed values running from "no sensation of pain" to "worst possible sensation of pain".

It is to be understood that the physical stimulus does not necessarily have to be an electrical current; it could also be a mechanical pressure or application of heat.

The above description is only to be regarded as advantageous embodiments of the invention, and the scope of the invention is only defined by the contents of the accompanying patent claims.

What is claimed is:

1. An apparatus for assessing a level of an arbitrary first sensation experienced by a person, the first sensation being compared to an induced physical sensation, the apparatus comprising:

a stimulator configured to supply a physical stimulus of an electrical current from a current source connected by a wiring with a first electrode and a second electrode to the person and to thereby induce a physical sensation in the person;

a stimulation level control device configured to control a level of said physical stimulus;

an activator mechanism, configured to activate a supply of said physical stimulus;

a deactivator mechanism actuateable by the person and configured to deactivate an assessment of said level of an arbitrary first sensation;

a registration device configured to register a sensation level value dependent on the supplied physical stimulus and corresponding to said first experienced sensation in response to a deactivation by the person of said assessment when the induced physical sensation is perceived to be comparable to the first experienced sensation; and a resilient contact provided between said electrodes and said wiring such that a predetermined pressure against said electrodes is required to establish electrical contact for delivering electrical current to said electrodes, wherein:

said activator mechanism is configured such that delivery of said electrical current is activated in response to the electrodes being connected in a closed electrical circuit, and deactivated when the closed circuit is interrupted, the registration device is configured such that said sensation level value dependent on the level of the electrical current is registered by the registration device in response to said interruption of the circuit.

2. The apparatus as recited in claim 1, further comprising a support structure for said electrodes, the electrodes being positioned on said support structure such that the electrodes are configured to be pressed against a body part of said patient and thereby achieve a closed current circuit for the electrical current stimulus.

3. The apparatus as recited in claim 2, wherein the electrodes are positioned on opposite sides of said support structure such that the electrodes are configured to be grasped between fingers of the person.

4. The apparatus as recited in claim 3, wherein the support structure is portable, elongate, and configured such that a force between fingers grasping the electrodes required to maintain said support structure in a specific position corresponds to a predetermined minimum pressure.

5. The apparatus as recited in claim 2, wherein the electrodes are positioned close to each other on one side of said support structure such that the electrodes are configured to be applied to an arbitrary part of a body of the person.

6. The apparatus as recited in claim 1, further comprising memory circuits configured to register said sensation level value, together with date and time data.

7. The apparatus as recited in claim 1, further comprising:

a display configured to display a registered sensation level value; and a value switch configured to activate a presentation of said sensation level value on said display.

8. The apparatus as recited in claim 1, further comprising an interface configured to enable transfer of said sensation level values to a computer for analysis and processing.

9. The apparatus as recited in claim 1, wherein the electrical current source starts to supply the physical stimulus automatically in response to the electrodes being short-circuited.

10. The apparatus as recited in claim 1, further comprising an electrical current source of a battery and means for upwards voltage transformation.

11. The apparatus as recited in claim 1, further comprising a microprocessor configured to control components of said apparatus.

12. The apparatus as recited in claim 1, wherein the stimulation level control device increases the electrical current in an arbitrary predetermined fashion, increasing in steps in one of a linear or exponential manner.

13. The apparatus as recited in claim 1, wherein said registration device registers said sensation level value on a scale ranging from one of 0–10, 0–60, or 0–99.

14. The apparatus as recited in claim 1, further comprising a system for signaling time for performing an assessment.

15. The apparatus as recited in claim 1, wherein the sensation to be assessed is one of pain or nausea.

16. The apparatus as recited in claim 1, wherein the induced physical sensation is pain.

17. The apparatus as recited in claim 1, wherein the supply of said stimulation is increased during an assessment.

18. An apparatus for assessing a level of an arbitrary first sensation experienced by a person, the first sensation being compared to an induced physical sensation, the apparatus comprising:

a stimulator configured to supply a physical stimulus from a stimulus source connected with a first stimulus electrode and a second stimulus electrode to the person and to thereby induce a physical sensation in the person;

a stimulation level control device configured to control a level of said physical stimulus;

an activator mechanism, configured to activate a supply of said physical stimulus;

a deactivator mechanism actuateable by the person and configured to deactivate an assessment of said level of an arbitrary first sensation;

a registration device configured to register a sensation level value dependent on the supplied physical stimulus and corresponding to said first experienced sensation in response to a deactivation by the person of said assessment when the induced physical sensation is perceived to be comparable to the first experienced sensation; and a resilient contact provided between said stimulus electrodes and an electrical wiring such that a predetermined pressure against said stimulus electrodes is required to establish a closed electrical circuit for delivering a stimulus to said stimulus electrodes, wherein:

said activator mechanism is configured such that delivery of heat is activated in response to the stimulus electrodes being connected in a closed electrical circuit, and deactivated when the closed circuit is interrupted, the registration device is configured such that a sensation level value dependent on the level of the heat is registered by the registration device in response to said interruption of the circuit.

19. The apparatus as recited in claim 18, further comprising a support structure for said stimulus electrodes, the stimulus electrodes being positioned on said support structure such that the stimulus electrodes are configured to be pressed against a body part of the person and thereby achieve a predetermined application of the stimulus to a body of the person.

20. The apparatus as recited in claim 19, wherein the stimulus electrodes are positioned on opposite sides of said support structure such that the stimulus electrodes are configured to be grasped between fingers of the person.

21. The apparatus as recited in claim 20, wherein the support structure is portable, elongate, and configured such that a force between fingers grasping the stimulus electrodes required to maintain said support structure in a specific position corresponds to a predetermined minimum pressure.

22. The apparatus as recited in claim 19, wherein the stimulus electrodes are positioned close to each other on one side of said support structure such that the stimulus electrodes are configured to be applied to an arbitrary part of a body of the person.

23. The apparatus as recited in claim 18, further comprising memory circuits configured to register said sensation level value, together with date and time data.

24. The apparatus as recited in claim 18, further comprising:

a display configured to display a registered sensation level value; and a value switch configured to activate a presentation of said sensation level value on said display.

25. The apparatus as recited in claim 18, further comprising an interface configured to enable transfer of said sensation level values to a computer for analysis and processing.

26. The apparatus as recited in claim 18, wherein the stimulus source starts to supply the physical stimulus automatically in response to a closed electrical circuit being established over the stimulus electrodes.

27. The apparatus as recited in claim 18, further comprising an electrical current source of a battery and means for upwards voltage transformation.

28. The apparatus as recited in claim 18, further comprising a microprocessor configured to control components of said apparatus.

29. The apparatus as recited in claim 18, wherein the stimulation level control device increases the stimulus in an arbitrary predetermined fashion, increasing in steps in one of a linear or exponential manner.

30. The apparatus as recited in claim 18, wherein said registration device registers said sensation level value on a scale ranging from one of 0–10, 0–60, or 0–99.

31. The apparatus as recited in claim 18, further comprising a system for signaling time for performing an assessment.

32. The apparatus as recited in claim 18, wherein the sensation to be assessed is one of pain or nausea.

33. The apparatus as recited in claim 18, wherein the induced physical sensation is pain.

34. The apparatus as recited in claim 18, wherein the supply of said stimulation is increased during an assessment.

35. An apparatus for assessing a level of an arbitrary first sensation experienced by a person, the first sensation being compared to an induced physical sensation, the apparatus comprising:

a stimulator configured to supply a physical stimulus of an electrical current from a current source connected by a wiring with a first electrode and a second electrode to the person and to thereby induce a physical sensation in the person;

a stimulation level control device configured to control a level of said physical stimulus;

an activator mechanism, configured to activate a supply of said physical stimulus;

a deactivator mechanism actuateable by the person and configured to deactivate an assessment of said level of an arbitrary first sensation;

a registration device configured to register a sensation level value dependent on the supplied physical stimulus and corresponding to said first experienced sensation in response to a deactivation by the person of said assessment when the induced physical sensation is perceived to be comparable to the first experienced sensation; and a resilient contact provided between said electrodes and said wiring such that a predetermined pressure against said electrodes is required to establish electrical contact for delivering electrical current to said electrodes, wherein the electrical current source starts to supply the physical stimulus automatically in response to the electrodes being short-circuited.

36. An apparatus for assessing a level of an arbitrary first sensation experienced by a person, the first sensation being compared to an induced physical sensation, the apparatus comprising:

a stimulator configured to supply a physical stimulus from a stimulus source connected with a first stimulus electrode and a second stimulus electrode to the person and to thereby induce a physical sensation in the person;

a stimulation level control device configured to control a level of said physical stimulus;

an activator mechanism, configured to activate a supply of said physical stimulus;

a deactivator mechanism actuateable by the person and configured to deactivate an assessment of said level of an arbitrary first sensation;

a registration device configured to register a sensation level value dependent on the supplied physical stimulus and corresponding to said first experienced sensation in response to a deactivation by the person of said assessment when the induced physical sensation is perceived to be comparable to the first experienced sensation; and a resilient contact provided between said stimulus electrodes and an electrical wiring such that a predetermined pressure against said stimulus electrodes is required to establish a closed electrical circuit for delivering a stimulus to said stimulus electrodes, wherein the stimulus source starts to supply the physical stimulus automatically in response to a closed electrical circuit being established over the stimulus electrodes.

* * * * *

UNITED STATES PATENT AND TRADEMARK OFFICE
CERTIFICATE OF CORRECTION

PATENT NO. : 6,709,406 B2
DATED : March 23, 2004
INVENTOR(S) : Laserow

It is certified that error appears in the above-identified patent and that said Letters Patent is hereby corrected as shown below:

<u>Title page,</u>
Item [30], Foreign Application Priority Data, should read:
-- [30]          Foreign Application Priority Data
Jan. 2, 1996     (SE) ............................. 9600009-6 --

Signed and Sealed this

Twenty-fifth Day of May, 2004

JON W. DUDAS
*Acting Director of the United States Patent and Trademark Office*